(12) United States Patent
Balthasart et al.

(10) Patent No.: US 6,720,435 B2
(45) Date of Patent: Apr. 13, 2004

(54) OXIRANE PRODUCTION METHOD

(75) Inventors: Dominique Balthasart, Brussels (BE); Michel Strebelle, Brussels (BE); Jean-Pierre Catinat, Waudrez (BE)

(73) Assignee: Solvay, Brussels (BE)

( * ) Notice: Subject to any disclaimer, the term of this patent is extended or adjusted under 35 U.S.C. 154(b) by 0 days.

(21) Appl. No.: 10/311,305

(22) PCT Filed: Jun. 26, 2001

(86) PCT No.: PCT/EP01/07272
§ 371 (c)(1), (2), (4) Date: Dec. 27, 2002

(87) PCT Pub. No.: WO02/00636
PCT Pub. Date: Jan. 3, 2002

(65) Prior Publication Data
US 2003/0158431 A1 Aug. 21, 2003

(30) Foreign Application Priority Data
Jun. 28, 2000 (FR) .............................. 00 08356

(51) Int. Cl.$^7$ ...................... C07D 301/12; C07D 301/19
(52) U.S. Cl. ....................... 549/531; 549/529
(58) Field of Search ................................. 549/531, 529

(56) References Cited

FOREIGN PATENT DOCUMENTS

| | | |
|---|---|---|
| EP | 0 659 473 | 6/1995 |
| EP | 0 919 551 | 6/1999 |
| EP | 0 930 308 | 7/1999 |
| FR | 1 440 125 | 8/1966 |
| WO | 98 28072 | 7/1998 |
| WO | 99/24164 | 5/1999 |
| WO | 99 28029 | 6/1999 |
| WO | 99/48882 | 9/1999 |
| WO | 99/48883 | 9/1999 |
| WO | 00/31057 | 6/2000 |

OTHER PUBLICATIONS

Perry's Chemical Engineers' Handbook, 6$^{th}$ Ed. pp. 4–25, 4–26, 20–3, and 20–58 to 20–75, 1984.

*Primary Examiner*—Ba K. Trinh
(74) *Attorney, Agent, or Firm*—Oblon, Spivak, McClelland, Maier & Neustadt, P.C.

(57) ABSTRACT

Process for manufacturing an oxirane in a reactor containing a liquid reaction medium, according to which an olefin is reacted, in a liquid reaction medium, with a peroxide compound in the presence of a solvent and in the presence of a solid catalyst which is used in the form of particles, at least some of which are in fluidized form in the reactor.

10 Claims, No Drawings

OXIRANE PRODUCTION METHOD

The present invention relates to a process for manufacturing oxirane by reacting an olefin with a peroxide compound in a liquid medium containing a solid catalyst. The invention relates in particular to the manufacture of propylene oxide or epichlorohydrin by epoxidation of propylene or allyl chloride using hydrogen peroxide.

It is known practice to manufacture propylene oxide by reaction between propylene and hydrogen peroxide in the presence of titanium silicalite as catalyst. For example, in patent application EP-A-0 659 473, such a process is performed in a reactor containing a fixed bed of the catalyst.

It is moreover known that the activity of catalysts of the titanium silicalite type in this type of manufacture falls over time. Consequently, it is necessary to separate the catalyst from the reaction medium regularly in order to be able to regenerate or replace it.

In the process disclosed in patent application EP-A-0 659 473, the catalyst in the form of a fixed bed is difficult to remove from the reactor to regenerate or replace it.

The present invention is directed towards overcoming this drawback by providing a novel process for manufacturing oxirane, in which the catalyst is easy to separate from the reaction medium. Another objective of the present invention is to provide a process which, when performed on an industrial scale, makes it possible to discharge the heat of reaction easily. This would make it possible to work at a high reaction rate, resulting in increased production efficiency.

The invention consequently relates to a process for manufacturing an oxirane in a reactor containing a liquid reaction medium, according to which an olefin is reacted, in the liquid reaction medium, with a peroxide compound in the presence of a solid catalyst and in the presence of a solvent; according to the invention, the solid catalyst is used in the form of particles and at least a portion of the particles in the reactor are in fluidized form.

One of the essential characteristics of the process according to the invention lies in the use of the catalyst in the form of particles in fluidized form. The fact that a fluid bed of particles can be used in an epoxidation reaction, in liquid medium, of an olefin with a peroxide compound in the presence of a solvent is surprising. The reason for this is that it is not established that particles of epoxidation catalyst tolerate fluidization, since these particles, by their nature, are fragile and risk being crushed or broken under the effect of the fluidization. The Applicant has now found, surprisingly, that these particles withstand fluidization without substantial loss of catalytic activity, showing little attrition and little breaking of grains. The fact that these particles can be used in fluidized form has the advantage, compared with a fixed bed, that the catalyst is easier to remove from the reactor in order to regenerate or replace it. In addition, a fluid bed regime ensures good heat exchange and thus better control of the reaction temperature and ensures a homogeneous dispersion of the catalyst in the liquid reaction medium.

The principles underlying the functioning of a fluid bed regime are described in "Perry's Chemical Engineers' Handbook, Sixth Edition", 1984, pages 4–25, 4–26, 20–3 and from 20–58 to 20–75.

In the context of the present invention, the term "fluidized form" means that the catalyst particles are in continuous motion, which is not the case in a fixed bed in which the catalyst remains immobile throughout the reaction. However, the motion of the particles is limited since they remain in a zone of the reactor, referred to as the fluid bed, which is between a zone of distribution of the fluid and a zone of fall-out of the solid particles. Thus, in principle, the particles do not leave the zone of the fluid bed throughout the reaction, which is not the case in a transported bed in which the particles are entrained to all the areas of the reactor.

The fluid distribution zone contains a distributor which serves to present preferential streams of the fluid and thus to ensure a homogeneous fluid stream. The distributor generally consists of a distribution plate or a grille. The fall-out zone of the solid particles serves to stop the movement of the solid catalyst particles.

Generally, the fluidized form of the catalyst particles is ensured by a fluid which moves in the reactor from the bottom upwards so as to create an ascending stream having a rising speed such that the catalyst particles are fluidized. Preferably, this fluid is a liquid. It advantageously consists of the liquid reaction medium which contains the olefin, the peroxide compound, the solvent, which is usually water, some of the oxirane produced, and possibly by-products formed during the reaction.

Several factors contribute towards the satisfactory functioning of the fluid bed regime. Mention may be made in particular of the choice of distributor, the rising speed of the fluid, the specific weight of the catalyst particles, the diameter of the catalyst particles, the dimensions of the reactor and the height of the fluid bed. All these parameters are mutually dependent. Consequently, in order to achieve a satisfactory functioning of the fluid bed, it is necessary to select an optimum combination of parameters which can keep the catalyst in fluidized form throughout the reaction.

In the process according to the invention, any known type of suitable distributor may be used.

The rising speed of the ascending fluid is usually greater than or equal to 0.01 m/min, in particular greater than or equal to 0.05 m/min. This speed is commonly less than or equal to 10 m/min, in particular less than or equal to 5 m/min.

The catalyst particles generally have an apparent specific weight, measured by free flow in air, of greater than or equal to 0.1 g/cm$^3$, in particular greater than or equal to 0.5 g/cm$^3$. The apparent specific weight is usually less than or equal to 2 g/cm$^3$ and more particularly less than or equal to 1 g/cm$^3$.

The catalyst particles commonly have a diameter of greater than or equal to 100 $\mu$m and in particular greater than or equal to 200 $\mu$m. The mean diameter is generally less than or equal to 5000 $\mu$m and in particular less than or equal to 2000 $\mu$m.

The catalyst advantageously contains a reduced fraction of fine particles having a diameter of less than 100 $\mu$m, since these fines are easily entrained out of the fluid bed and thus result in a loss of catalyst, fouling of the plant or the appearance of uncontrolled side reactions. In general, the fraction of fines is less than or equal to 5% by weight of the catalyst and in particular less than or equal to 2% by weight, for example less than or equal to 0.1% by weight.

The catalyst particles used in the process according to the invention generally contain a binder and an active element. The amount of binder is generally greater than or equal to 1% by weight of the catalyst, in particular greater than or equal to 10%. The binder content is usually less than or equal to 90% by weight of the catalyst and in particular less than or equal to 60% by weight.

The active element is generally as zeolite and preferably a titanium zeolite. The term "titanium zeolite" is intended to denote a solid containing silica which has a microporous crystal structure of zeolite type and in which several silicon atoms are replaced with titanium atoms. The titanium zeolite advantageously has a crystal structure of ZSM-5, ZSM-11, ZSM-12, MCM-41 or ZSM-48 type. It may also have a crystal structure of beta zeolite type, preferably free of aluminum. Zeolites with an infrared absorption band at about 950–960 cm$^{-2}$ are suitable for use. Titanium zeolites or silicalite type are preferred. Those corresponding to the formula $xTiO_2(1-x)SiO_2$ in which x is from 0.001 to 0.5 and preferably from 0.001 to 0.05 give high performance. Materials of this type, known under the name TS-1, have a microporous crystalline zeolite structure similar to that of zeolite ZSM-5.

The binder generally comprises one or more silicon derivatives.

The catalyst particles may be obtained by any known means, for example by extrusion, as disclosed in patent application WO 99/28029 by the Applicant, the content of which is incorporated by reference in the present patent application, or by a spray process, as disclosed in patent application WO 99/24164 by the Applicant, the content of which is also incorporated by reference in the present patent application.

In a first embodiment of the process according to the invention, the reactor consists of several tubular reactors arranged in parallel in a heat exchanger, each reactor containing a fluid bed of catalyst particles. In general, the tubular reactors are fed in parallel with a single source of liquid reaction medium containing the olefin, the peroxide compound and the solvent. This single source may also contain recycled traces of oxirane formed and/or of by-products. The heat exchanger advantageously consists of a chamber filled with coolant liquid, into which the tubular reactors are immersed. An alternative solution consists in circulating in the said chamber the coolant liquid which may be kept at a sufficient pressure so as not to change state (and simply heat up) or may be partially vaporized.

This first embodiment is found to be particularly advantageous since it makes it possible to ensure equivalent conditions (in particular the depressurization) in each tubular reactor more easily when compared with a process which uses the catalyst in a fixed bed. In addition, it makes it possible to work in reaction tubes of small size, even at the industrial scale. In reactors of small size, it is easier to obtain a homogeneous dispersion of the catalyst since, in a large reactor, the probability of creating preferential streams in certain areas of thee reactor is greater. Small-sized reactors also make it possible to work at a higher reaction rate while at the same time avoiding the formation of by-products. Specifically, it has been found that the oxirane formed can undergo, in the epoxidation reaction medium, hydrolysis and alcoholysis side reactions (methanolysis when methanol is used as solvent) to form by-products. In a small-sized reactor, the contact between the oxirane formed and water or the solvent is minimized compared with a large reactor.

In a second embodiment of the process according to the invention, the reactor consists of a single chamber containing the liquid reaction medium and the catalyst in fluidized form, into which are immersed one or more tubes arranged side by side and through which passes a coolant liquid. An alternative solution consists in circulating in the said tubes the coolant liquid which may be kept at a sufficient pressure so as not to change state (and simply heat up) or may be partially vaporized.

These two embodiments make it possible easily to remove the heat of reaction formed during the epoxidation by heating and/or evaporation of the coolant liquid.

The solvent used in the process according to the invention may be chosen from saturated, linear or branched aliphatic alcohols. The alcoholic solvent generally contains up to 10 carbon atoms, preferably from 1 to 6 carbon atoms. Examples which may be mentioned are methanol and ethanol. Methanol is preferred.

The epoxidation reaction medium usually also contains water.

The amount of solvent used in the process according to the invention is generally at least 25% by weight of the liquid reaction medium, in particular at least 40% by weight, for example at least 50% by weight. This amount usually does not exceed 99% by weight and in particular does not exceed 95% by weight.

The molar ratio between the amounts of olefin and of peroxide compound used in the process according to the invention is generally at least 0.1, in particular at least 0.2 and preferably at least 0.5. This molar ratio is usually not more than 100, in particular not more than 50 and preferably not more than 25.

The process according to the invention may be continuous or batchwise. It may be carried out in only one reactor or in several reactors arranged in series. In a process in several reactors, it may prove to be advantageous to introduce the peroxide compound only into the first reactor, as disclosed in the Applicant's patent application filed on the same day as the present patent application and entitled "Process for the manufacturing oxirane using a peroxide compound" (the content of which is incorporated by reference). In addition, each reactor may be followed by a distillation column to separate the oxirane formed from the reaction medium, before introducing it into the next reactor, as disclosed in the Applicant's patent application filed on the same day as the present patent application and entitled "Process for manufacturing oxirane comprising the separation of the oxirane from the reaction medium" (the content of which is incorporated by reference).

In the process according to the invention, when it is carried out continuously, the peroxide compound is generally used in an amount of at least 0.005 mol per hour and per gram of catalyst, in particular of at least 0.01 mol per hour and per gram of catalyst. The mount of peroxide compound is usually less than or equal to 25 mol per hour and per gram of catalyst and in particular less than or equal to 10 mol per hour and per gram of catalyst. Preference is shown for an amount of peroxide compound of greater than or equal to 0.03 mol per hour and per gram of catalyst and less than or equal to 2.5 mol per hour and per gram of catalyst.

In the process according to the invention, the peroxide compound is advantageously used in the form of an aqueous solution. In general, the aqueous solution contains at least 2% by weight of peroxide compound and in particular at least 5% by weight. It usually contains not more than 90% by weight of peroxide compound and in particular not more than 70% by weight.

The reaction temperature between the olefin and the peroxide compound may range from 10° C. to 125° C. In one advantageous variant as disclosed in patent application EP 99/08703 by the Applicant, it is greater than 35° C. to overcome the gradual deactivation of the catalyst. The temperature may be greater then or equal to 40° C. and preferably greater than or equal to 45° C. A temperature of greater than or equal to 50° C. is more particularly preferred. The reaction temperature is preferably less than 100° C.

In the process according to the invention, the reaction between the olefin and the peroxide compound may take place at atmospheric pressure. It may also be performed under pressure. This pressure generally does not exceed 40 bar. A pressure of 20 bar is suitable in practice.

The peroxide compounds which may be used in the process according to the invention are peroxide compounds containing one or more peroxide functions (—OOH) which may release active oxygen and which are capable of carrying out an epoxidation. Hydrogen peroxide and peroxide compounds which may produce hydrogen peroxide under the conditions of the epoxidation reaction are suitable for use. Hydrogen peroxide is preferred.

When hydrogen peroxide is used, it may be advantageous to use, in the process according to the invention, an aqueous hydrogen peroxide solution in crude form, i.e. in unpurified form. For example, a solution obtained by simple extraction with substantially pure water of the mixture derived from the oxidation of at least one alkylanthrahydroquinone (process known as "autoxidation AO process") without a subsequent washing and/or purification treatment may be used. These crude hydrogen peroxide solutions generally contain from 0.001 to 10 g/l of organic impurities expressed as TOC (Total Organic Carbon). They usually contain metal cations (such as alkali metals or alkaline-earth metals, for instance sodium) and anions (such as phosphates and nitrates) in contents of from 0.01 to 10 g/l.

In another variant of the process, a hydrogen peroxide solution produced by direct synthesis using oxygen and hydrogen in the presence of methanol may be used.

The oxirane which may be prepared by the process according to the invention is an organic compound comprising a group corresponding to the general formula:

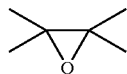

The oxirane generally contains from 2 to 10 carbon atoms, preferably from 3 to 6 carbon atoms. The oxiranes which may be prepared advantageously by the process according to the invention are 1,2-epoxypropane and 1,2-epoxy-3-chloropropane. The preferred oxirane is 1,2-epoxypropane.

The olefins which are suitable in the process according to the invention generally contain from 2 to 10 carbon atoms and preferably 3 to 6 carbon atoms. Propylene, butylene and allyl chloride are suitable for use. Propylene and allyl chloride are preferred. Propylene is most particularly preferred.

In the process according to the invention, a gas which has no negative effect on the epoxidation reaction may also be fed into the reactor. Specifically, in patent application WO 99/48883 (the content of which is incorporated by reference into the present patent application), the Applicant found that by introducing a gaseous compound into the reaction medium at a flow rate which is sufficient to allow the oxirane produced to be entrained and removed from the reactor at the same time as the gaseous compound, the contact time between the oxirane produced and the epoxidation reaction medium is reduced. The formation of by-products is thus also avoided and the selectivity towards epoxidation is increased. Another variant consists in separating the oxirane formed from the liquid reaction medium by distillation in a distillation column.

In the process according to the invention, it may prove to be advantageous to monitor the pH of the liquid phase. For example, it may be advantageous to maintain the pH of the liquid phase during the reaction between the olefin and the peroxide compound at a value of from 4.8 to 6.5, for example by adding a base (sodium hydroxide) to the epoxidation medium, as recommended in patent application WO 99/48882 by the Applicant (the content of which is incorporated by reference into the present patent application).

The reaction between the olefin and the peroxide compound may be carried out in the presence of a salt such as sodium chloride, as disclosed in patent application WO EP 99/08703 by the Applicant (the content of which is incorporated by reference into the present patent application).

It may be advantageous to introduce the olefin into the reactor, in which the epoxidation reaction has taken place, in a form diluted in one or more alkanes. For example, a fluid containing the olefin and also at least 10% (in particular 20%, for example at least 30%) by volume of one or more alkanes may be introduced into the epoxidation reactor. For example, in the case of propylene, the latter may be mixed with at least 10% by volume of propane when the recycled unconverted propylene is introduced into the reactor. It may also be a source of propylene which is not completely freed of propane.

What is claimed is:

1. A process for manufacturing an oxirane in a reactor containing a liquid reaction medium, according to which an olefin is reacted, in the liquid reaction medium, with a peroxide compound in the presence of a solid catalyst and in the presence of a solvent, and according to which the solid catalyst is used in the form of particles and at least a portion of the particles in the reactor are in fluidized form.

2. The process according to claim 1, in which the liquid reaction medium containing the olefin, the peroxide compound, the solvent, the oxirane formed and possibly by-products moves in the reactor from the bottom upwards so a to create an ascending stream having a rising speed such that the catalyst particles are fluidized.

3. The process according to claim 1, in which the catalyst particles have an apparent specific weight, measured by free flow in air, of from 0.1 to 2 g/cm$^3$.

4. The process according to claim 1, in which the catalyst particles have a diameter of from 100 to 5000 $\mu$m.

5. The process according to claim 1, in which the rising speed of the liquid reaction medium is from 0.01 to 10 m/min.

6. The process according to claim 1, in which the reactor consists of several tubular reactors arranged in parallel in a heat exchanger in which they are fed with a single source of liquid reaction medium containing the olefin, the peroxide compound and the solvent.

7. The process according to claim 6, in which the single source also contains recycled traces of the oxirane formed and/or of by-products.

8. The process according to claim 1, in which the heat of the reaction is removed by circulation of a coolant fluid surrounding the tubular reactors.

9. The process according to claim 1, in which the reactor consists of a single chamber containing the liquid reaction medium and the catalyst in fluidized form, into which are immersed several tubes arranged side by side and through which passes a coolant fluid.

10. The process according to claim 1, in which the oxirane is propylene oxide or epichlorohydrin, the olefin is propylene or allyl chloride, the peroxide compound is hydrogen peroxide, the catalyst contains titanium silicalite and the solvent is methanol.

* * * * *

UNITED STATES PATENT AND TRADEMARK OFFICE
CERTIFICATE OF CORRECTION

PATENT NO. : 6,720,435 B2
DATED : April 13, 2004
INVENTOR(S) : Balthasart et al.

It is certified that error appears in the above-identified patent and that said Letters Patent is hereby corrected as shown below:

Title page,
Item [73], Assignee, should read:
-- [73]   Assignee:   Solvay (Societe Anonyme), Brussels (BE) --

Signed and Sealed this

Twelfth Day of July, 2005

JON W. DUDAS
*Director of the United States Patent and Trademark Office*